United States Patent
Swisher

(10) Patent No.: US 8,210,168 B2
(45) Date of Patent: Jul. 3, 2012

(54) GASTRIC INSERTION CONFIRMATION DEVICE AND METHOD OF USE

(75) Inventor: David Rork Swisher, St. Charles, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 344 days.

(21) Appl. No.: 12/545,439

(22) Filed: Aug. 21, 2009

(65) Prior Publication Data

US 2010/0081896 A1  Apr. 1, 2010

Related U.S. Application Data

(60) Provisional application No. 61/101,354, filed on Sep. 30, 2008.

(51) Int. Cl.
*A61M 16/00* (2006.01)
(52) U.S. Cl. ......... 128/202.22; 128/200.24; 128/207.15; 604/910
(58) Field of Classification Search .................. 604/910; 128/202.22, 205.23, 200.24, 200.27, 205.27, 128/205.28, 207.14, 207.15
See application file for complete search history.

(56) References Cited

U.S. PATENT DOCUMENTS

| | | | |
|---|---|---|---|
| 4,617,011 A | 10/1986 | Bloxom, Jr. | |
| 4,790,327 A | 12/1988 | Despotis | |
| 4,804,375 A | 2/1989 | Robertson | |
| 4,874,365 A | 10/1989 | Frederick et al. | |
| 4,879,999 A | 11/1989 | Leiman et al. | |
| 5,273,523 A | 12/1993 | Sozuki et al. | |
| 5,403,290 A | 4/1995 | Noble | |
| 5,415,165 A * | 5/1995 | Fiddian-Green | 600/573 |
| 5,487,731 A | 1/1996 | Denton | |
| 5,620,004 A | 4/1997 | Johansen | |
| 5,902,273 A | 5/1999 | Yang et al. | |
| 6,202,646 B1 | 3/2001 | Camodeca et al. | |
| 6,878,130 B2 | 4/2005 | Fournie et al. | |
| 7,178,519 B2 | 2/2007 | Melker et al. | |
| 2003/0109848 A1 | 6/2003 | Fleeman | |
| 2006/0060202 A1 * | 3/2006 | Flynn et al. | 128/207.14 |
| 2006/0129092 A1 * | 6/2006 | Hanlon et al. | 604/93.01 |
| 2008/0004598 A1 | 1/2008 | Gilbert | |
| 2008/0210235 A1 * | 9/2008 | Field et al. | 128/202.22 |

OTHER PUBLICATIONS

European Search Report regarding related application serial No. EP 09170467.6 dated Jan. 14, 2010, 6 pgs.

\* cited by examiner

*Primary Examiner* — Laura Bouchelle
(74) *Attorney, Agent, or Firm* — Elias Domingo, Esq.

(57) ABSTRACT

A confirmation device. The device includes a housing having a central passageway and a secondary passageway extending from the central passageway. The device also has a negative pressure member in communication with the secondary passageway and an indicator mechanism in fluid communication with the secondary passageway for visually indicating the presence of one or more components within the secondary passageway. The negative pressure member is operable to draw fluid across the indicator mechanism.

14 Claims, 10 Drawing Sheets

GASTRIC INSERTION CONFIRMATION DEVICE AND METHOD OF USE

CROSS-REFERENCE TO RELATED APPLICATIONS

The present application is a non-provisional of U.S. Patent Application Ser. No. 61/101,354, filed Sep. 30, 2008, and entitled, "Gastric Insertion Confirmation Device and Method of Use", which is hereby incorporated by reference in its entirety.

FIELD OF THE INVENTION

The present disclosure relates generally to gastric tubing assemblies. More particularly, the present disclosure relates to a device for confirming the entry of gastric tubing within the gastrointestinal tract.

BACKGROUND OF THE INVENTION

Medical systems inserted within a body of a patient for the administration and/or removal of fluids from the patient, such as, for example, nasogastric tubing are known in the art. Nasogastric tubing is typically employed in hospitals, nursing homes, care facilities, etc. to remove fluids from the body of the patient, such as, for aspirating fluids from a gastrointestinal tract (GI tract) of the patient or to introduce nutrients, supplements, medicines, etc. to the patient.

In one application, nasogastric tubing aspirates fluid and air to decompress the contents of the patient's stomach to avoid damaging the inner wall, e.g., the gastric mucosa. Nasogastric tubing may also facilitate removal of accumulated fluids, such as blood from the GI tract due to disease, intestinal obstruction, bleeding ulcers, and paralytic ulcers to prevent progressive distension of the GI tract. Progressive distension of the GI tract can lead to shock, visceral injury, and vomiting. Vomit may be aspirated into the respiratory tract and cause asphyxia and pneumonia.

Nasogastric tubes are employed with patients undergoing abdominal surgery to keep the stomach vacant of fluid and postoperatively to prevent complications, such as decreased gastrointestinal function. Such nasogastric tubing advantageously prevents pooling of liquids in the GI tract to facilitate postoperative recovery of digestive function. Nasogastric tubing can also be employed to protect gastric suture lines, prevent and treat paralytic ileus, treat drug overdoses, lavage, as well as treat other conditions affecting the GI tract.

Conventionally, a flexible plastic nasogastric tube is used. The nasogastric tube defines a passageway extending from a proximal end to a distal end. A practitioner introduces the distal end of the nasogastric tube through a nasal canal of a patient via one nostril. The distal end of the tube is advanced through the pharynx and down the esophagus into the GI tract. To ensure the distal end of the tube is properly received within the GI tract, a first x-ray is taken after the distal end of the tube has passed the esophagus/trachea junction and a second x-ray is taken the tube is fully inserted in the GI tract. The need to take multiple x-rays during the insertion of the gastric tube within the GI tract is time consuming and adds to the expense of the procedure.

Therefore, it would be desirable to overcome the disadvantages and drawbacks of conventional apparatus using a confirmation device positioned along the tubing of a gastric tubing assembly for providing visual indication to a clinician that the distal end of the gastric tube is properly received within the GI tract of a patient without the need for multiple x-rays.

SUMMARY OF THE INVENTION

In one aspect of the present invention, a confirmation device comprises a housing having a central passageway and a secondary passageway extending from the central passageway. The confirmation device also includes a negative pressure member in communication with the secondary passageway and an indicator mechanism in fluid communication with the secondary passageway for visually indicating the presence of one or more components within the secondary passageway. The negative pressure member is operable to draw fluid across the indicator mechanism.

In another aspect, a confirmation device comprises a housing having a central passageway and a secondary passageway extending from the central passageway. The device includes a bellows mechanism in communication with the secondary passageway and including a bellows affixed to a portion of the housing. Further, the device comprises an indicator mechanism in fluid communication with the secondary passageway for visually indicating the presence of one or more components within the fluid flow in the secondary passageway. The indicator mechanism includes a color changing member configured to change color in the presence of one or more components. The bellows assembly is operable to draw fluid across the indicator mechanism.

In yet another aspect, the invention includes a confirmation device comprising a housing having a central passageway and a secondary passageway extending from the central passageway. The device also comprises a negative pressure member in communication with the secondary passageway and an indicator mechanism in fluid communication with the secondary passageway for visually indicating the presence of one or more components within fluid flow in the secondary passageway. In addition, the confirmation device includes an obstruction assembly configured to selectively obstruct flow through the central passageway.

Other objects and features will be in part apparent and in part pointed out hereinafter.

BRIEF DESCRIPTION OF THE DRAWINGS

Various embodiments of the presently disclosed medical device having a prefilled balloon are disclosed herein with reference to the drawings, wherein.

Corresponding reference characters indicate corresponding parts throughout the drawings.

DESCRIPTION OF THE PREFERRED EMBODIMENTS

Figure 1:
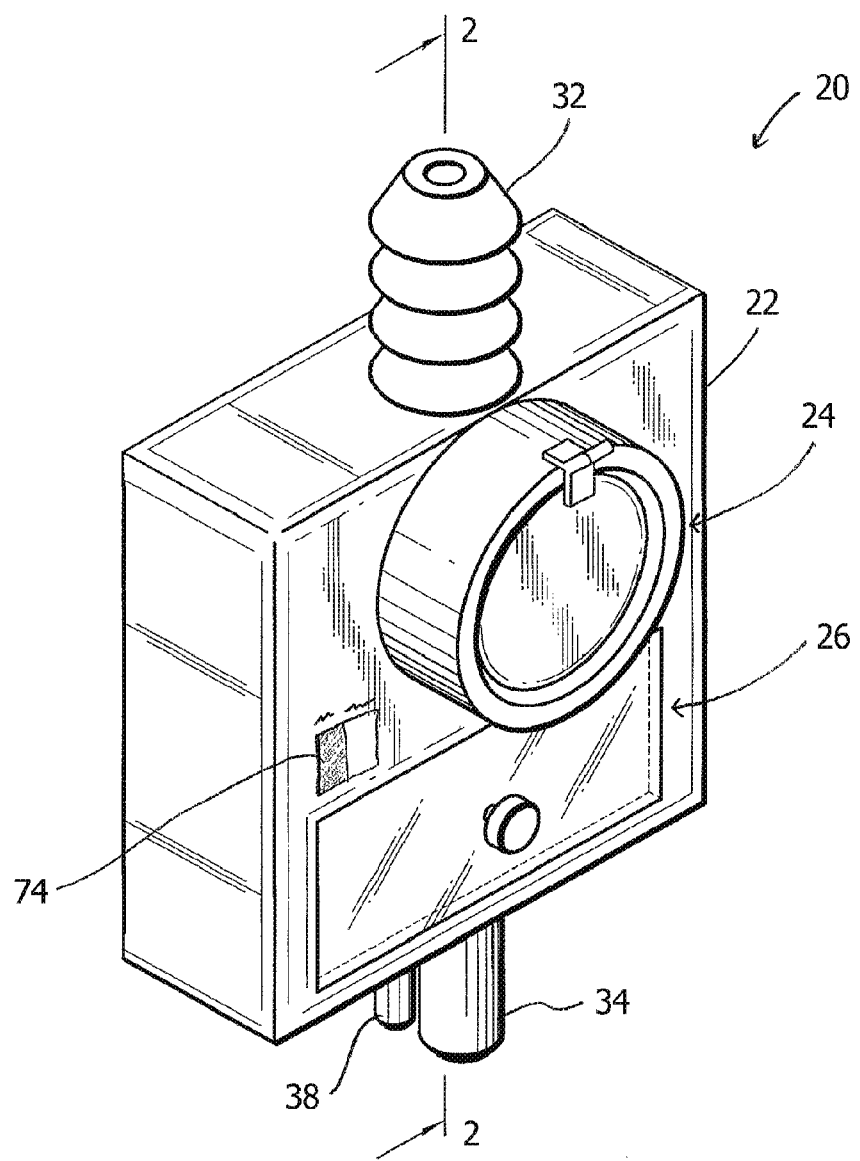
FIG. 1 is a perspective of a gastrointestinal insertion confirmation device according to a first embodiment of the present disclosure.

Referring initially to FIG. 1, a first embodiment of a gastrointestinal insertion confirmation device according to the present disclosure is designated in its entirety by the reference number 20. The confirmation device 20 includes a housing 22, a negative pressure member (generally designated by 24), an indicator assembly (generally designated by 26), a passageway obstruction assembly (generally designated by 28 in FIG. 2) and a vent mechanism (generally designated by 30 in FIG. 2). The confirmation device 20 is adapted to be placed along a flowpath of a gastric tubing assembly (not shown) to provide a clinician with a visual indication that a distal end (not shown) of the gastric tube 50 (FIG. 2) is positioned within a GI tract of a patient and has not been inadvertently inserted into a patient's trachea (not shown).

Figure 2:
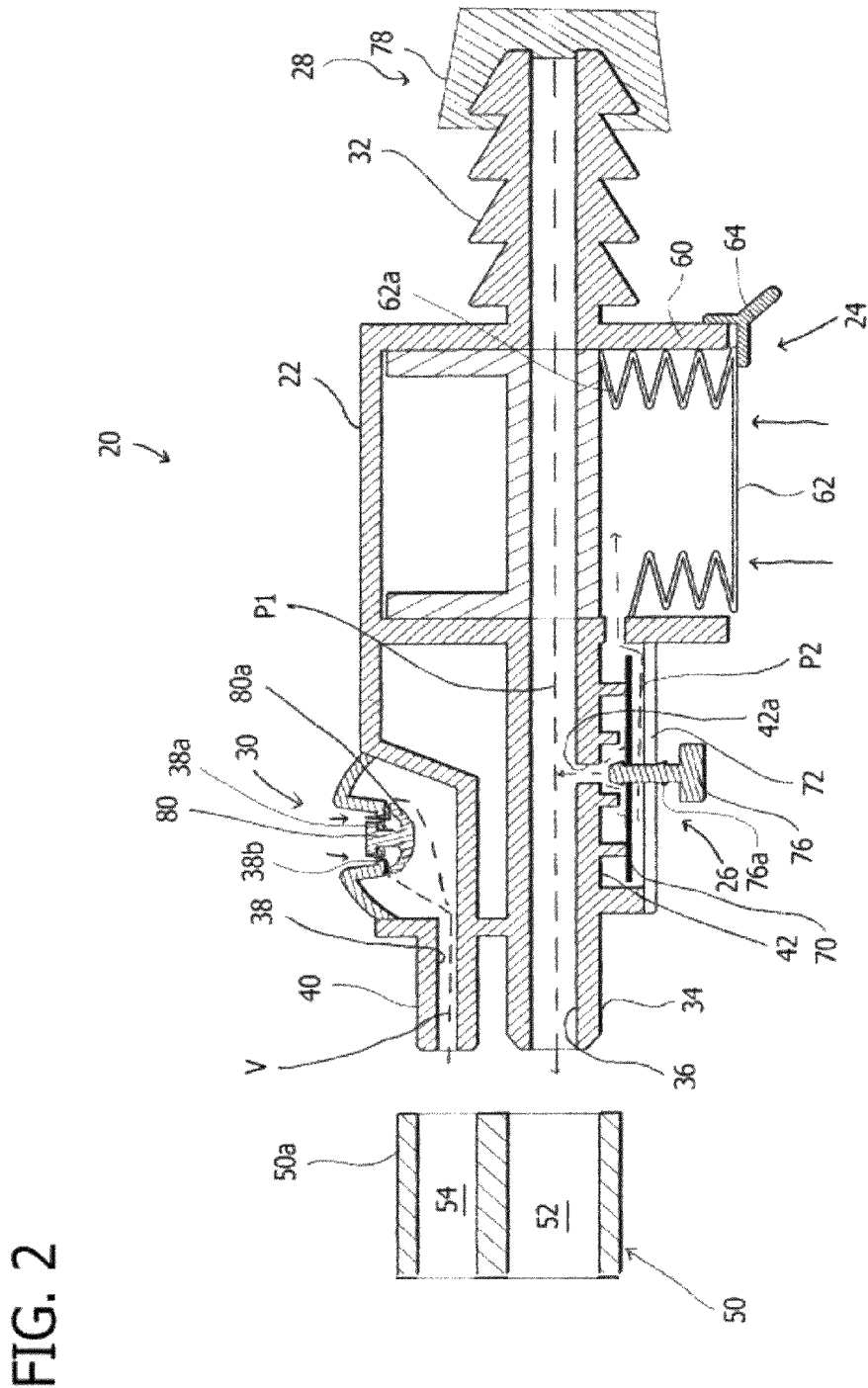
FIG. 2 is a cross section of the confirmation device of FIG. 1 taken along line 2-2 of FIG. 1 showing a bellows assembly in a second or compressed condition.

Referring to FIGS. 1 and 2, the housing 22 includes a proximal or upstream connector 32, a first distal or downstream connector 34 opposite the proximal connector, and a central passageway 36 extending between the proximal and distal connectors. The central passageway 36 forms a primary flowpath P1 through the housing 22. The housing 22 further includes a secondary passageway 38 having a second distal or downstream connector 40 formed at a first end. A second end of the secondary passageway 38 communicates with the vent mechanism 30. As will be discussed in further detail below, the secondary passageway 38 defines a vent path V through the housing 22. A third passageway 42 extends from the central passageway 36 and defines a secondary flowpath P2.

As illustrated in FIG. 2, the first and second distal connectors 34, 40 are configured to be received on a proximal end 50a of a gastric tube 50. As shown, the first distal connector 34 is configured for receipt within a first lumen 52 of the gastric tube 50, and the second distal connector 40 is configured for receipt within a second lumen 54 of the gastric tube. In an alternative embodiment, the first and second distal connectors 34, 40 are configured to engage separate tubes (not shown). The first and second distal connectors 34, 40 may be configured to engage the gastric tube 50 by a friction fit, as shown, or may instead include luer fittings, clamps, or other mechanical fasteners for selectively engaging the gastric tube. The proximal connector 32 of the housing 22 is configured to engage a tube, valve assembly, or other element (not shown) of a gastric tubing assembly. As shown, the proximal connector 34 comprises a friction fitting; however, other fittings may be employed, including luer, bayonet coupling, clamps, and other mechanical fasteners.

Figure 3:
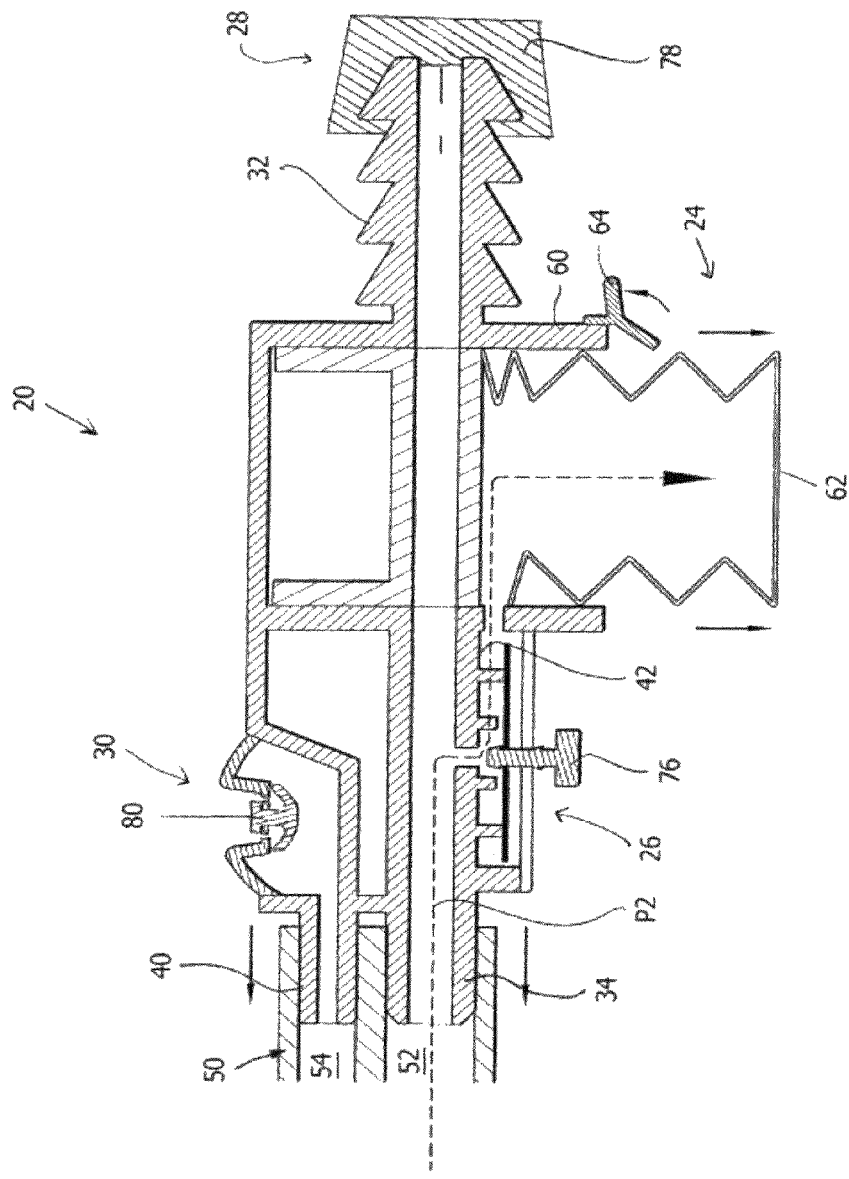
FIG. 3 is a cross section of the confirmation device of the first embodiment showing the bellows assembly in a first or expanded condition and the push-pin in an open position.

As shown in FIGS. 1 and 2, the negative pressure assembly 24 communicates with a second end of the third passageway 42. The third passageway 42 fluidly connects the negative pressure assembly 24 to the central passageway 36 along the secondary flowpath P2 (FIG. 3). The negative pressure assembly 24 includes a bellows assembly having a base 60 extending from housing 22. The base 60 is configured to selectively receive a bellows member 62. The base 60 may be integrally formed with the housing 22, as shown, or may be joined to the housing. The bellows member 62 is formed from a flexible and/or elastic material and is configured to be compressed by a clinician and to return to an uncompressed or expanded condition when released. An open first end 62a of the bellows member 62 is received within an inner portion of base 60. In a first or expanded condition (FIG. 3), the bellows member 62 is filled with air. Compressing the bellows member 62 forces air from within the bellows member. The base 60 is configured to receive the compressed bellows member 62 (FIG. 2) therein. A locking mechanism, for example latch 64, may be formed on an outer end of the base 60 to selectively retain the bellows member 62 within the base when bellows member is in a fully compressed condition. Subsequently releasing the latch 64 permits the bellows member 62 to expand within the base 60. In an alternative embodiment, the latch 64 may be omitted, in which case, a clinician is required to manually maintain the bellows member 62 in the compressed state within the base 60 until such time as expansion is desired. As the bellows member 62 expands, it creates suction within the third passageway 42 of the housing 22 along the secondary flowpath P2 to draw air from the central passageway 36 of the device 20 and the first lumen 52 of the gastric tube 50 over the indicator assembly 26. The size of the bellows member 62 may vary depending on the amount of air flow necessary to activate the indicator assembly 26, as will become apparent below.

As further illustrated in FIGS. 1 and 2, the indicator assembly 26 is formed within the third passage 42 of the housing 22. The indicator assembly 26 is configured to indicate certain gases are present within the secondary flowpath P2 that are found only within the GI tract or only within the trachea. For example, carbon-dioxide would be expected to be present in the trachea, but not in the GI tract. Methane, on the other hand, would be expected to be found in the GI tract, but not in the trachea. Thus, in one embodiment, the presence of carbon-dioxide in the secondary flowpath P2 indicates the distal end (not shown) of the gastric tube 50 is in the trachea of a patient, and not properly positioned in the GI tract.

The Indicator assembly 26 includes a color changing member 70 extending across the secondary flowpath P2. The color changing member 70 may include any of a number of known materials configured to change color in the presence of certain molecules. In a reusable embodiment, the color changing member 70 is further configured to revert back to an original color when the molecules are no longer present within the secondary flowpath P2. Alternatively, device 10 may include a replaceable color changing member 70. The indicator assembly 26 includes a clear cover 72 formed over the color changing member 70 to permit a clinician to view the color changing member 70. A color scale or legend 74 (FIG. 1) may be included on the housing 22 to provide a clinician with a reference for determining the meaning of the color of the color changing member 70. The indicator assembly 26 further includes a push-pin or plug 76 for preventing fluid from traveling between the third passageway 42 and the central passageway 36. The push-pin 76 is configured to obstruct the secondary path P2, thereby sealing the secondary path P2 from the primary flowpath P1. As shown, the push-pin 76 forms a plug configured to be received in an opening 42a connecting the central and third passageways 36 and 42, respectively. The push-pin 76 includes barbs or ridges 76a for permanently retaining the push-pin 76 in opening 42a.

As illustrated in FIGS. 2 and 3, the passageway obstruction assembly 28 includes an end cap 78. The end cap 78 is configured to be selectively connected to the proximal connector 32 during insertion and confirmation that the gastric tube 50 is received in the GI tract of a patient. The end cap 78 is configured to obstruct the central passageway 36, thereby preventing flow along the primary flowpath P1. In this manner, fluid in the central passageway 36 is diverted through the opening 42a in the housing 22 and into the third passageway 42.

As shown in FIG. 2, the vent mechanism 30 communicates with a distal end of the second passageway 38. The vent mechanism 30 is configured to permit external air to flow into the second passageway 38 when excessive negative pressure is experienced in the GI tract of a patient and experienced by the communication device 20 via the lumen 54 of the gastric tube 50. The vent mechanism 30 includes a vent member 80 positioned in an opening 38a formed in the housing 22. The housing 22 further includes vent openings 38b formed around the opening 38a. The vent member 80 includes a first umbrella-shaped sealing end 80a configured to engage the housing 22 and selectively seal the vent path V. When the negative pressure in the GI tract of a patient reaches a predetermined level, as experienced in the second passageway 38, the force acting on the first sealing end 80a of the vent member 80 causes the first sealing end to flex away from the housing 22, thereby uncovering the vents 38b formed in the housing 22 and permitting air to flow through vents into passageway 38. In this manner, the vent mechanism 30 reduces the excessive negative pressure within the GI tract of a patient. Once the excess negative pressure is reduced, the force acting on the first sealing end 80a of the vent member 80 subsides, allowing the first sealing end to return to an unflexed condition, resealing the first end against the openings 38b. In an alternative embodiment, the vent mechanism 30 may also be configured to prevent excess buildup of pressure within the GI tract of a patient. In this manner, the vent mechanism 30 would be configured to release excess pressure from the second passageway 38 to reduce the pressure within the GI tract of a patient.

Operation of the confirmation device 20 will now be described with reference to FIGS. 2-4. Referring initially to FIG. 2, once removed from its packaging (not shown), the confirmation device 20 is selectively secured to the proximal end 50a of the gastric tube 50. As discussed above, the gastric tube 50 includes the first lumen 72 configured to receive the first distal connector 34 of the housing 22 and the second lumen 74 configured to receive the second distal connector 40 of the housing 22. The confirmation device 20 may be packaged with the bellows member 62 of the bellows mechanism 24 in a compressed condition, otherwise, prior to insertion of the gastric tube 50 into a patient (not shown), the bellows member is compressed within the base 60 and retained therein by the latch 64. In an alternate embodiment without a latch, the clinician is required to manually maintain bellows member 62 in the compressed state. If the end cap 80 is not provided on the proximal connector 32, an end cap should be installed on the proximal connector 32 prior to the gastric tube 50 being inserted in the patient.

The gastric tube 50 is then inserted within a patient by advancing its distal end (not shown) down the esophagus of the patient. This may be accomplished nasogastrically. Once the clinician feels that the distal end of the gastric tube 50 is properly positioned in the GI tract, the clinician may use the confirmation device 20 to obtain a visual indication whether or not the gastric tube is properly positioned in the GI tract.

As illustrated in FIG. 3, releasing of the latch 64 permits the bellows member 62 to expand out from the base 60 returning to its original expanded condition. As noted above, expansion of the bellows member 62 causes suction along the flowpath P2 of the housing 22. This suction draws fluid surrounding the distal end (not shown) of the gastric tube 50 through the lumen 52, into the central passageway 36 and through the third passageway 42 past the indicator mechanism 26. The fluid passing the color changing member 70 of indicator mechanism 30 causes the color changing member 70 to change color depending on the composition of the gas. In one embodiment, if the color changing member 70 becomes purple, it indicates to the clinician that the distal end of the gastric tube 50 is properly received within the GI tract, but if the color changing member becomes yellow, this indicates the distal end of gastric tube is not in the GI tract and must be repositioned. The color scale or legend 74 on the housing 22 provides the clinician with a reference to determine the meaning of the color of the color changing member 70. Alternative embodiments may use alternate color combinations.

When the confirmation device 20 is configured for more than single use, the bellows member 62 may be recompressed within the base 60 if the color changing member 70 indicates that the gastric tube 50 is not properly positioned within the GI tract. The recompression of the bellows member 62 causes the air within the bellows member 62 to flow back past the color changing member 70, clearing from the third passageway 42 of fluid drawn from the patient. In this manner, the color changing member 70 returns to its original color. Once the confirmation device 20 has been reset and the distal end of the gastric tube 50 has been repositioned, the bellows member 62 may be released again to suction air from around the distal end of the gastric tube 50 past the color changing member 70. This process may be repeated as necessary, until the distal end of the gastric tube 50 is properly positioned within the GI tract of the patient.

Figure 4:
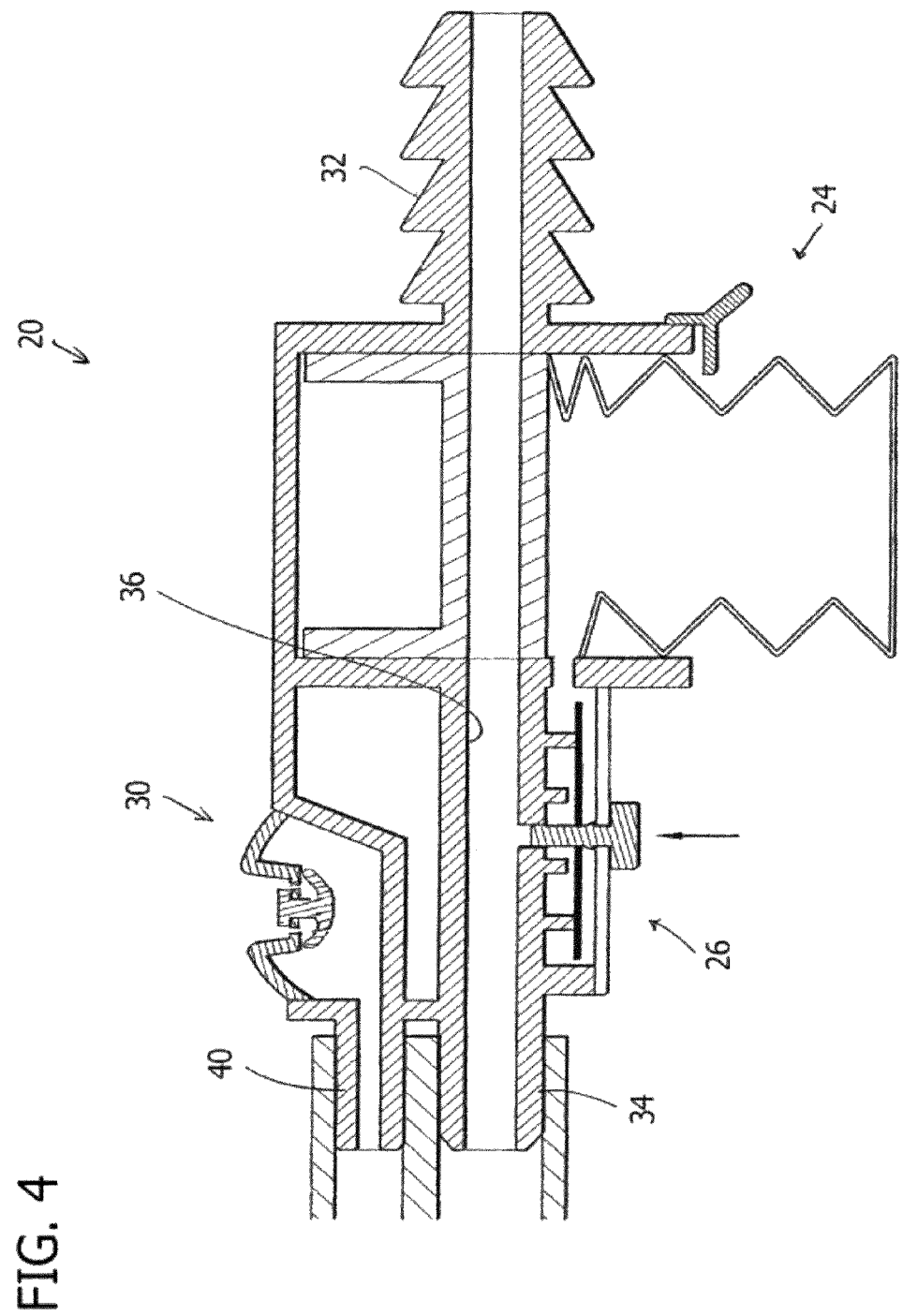
FIG. 4 is a cross section of the confirmation device of the first embodiment showing the bellows assembly in the expanded condition and the push-pin in a closed position.

Referring now to FIG. 4, once the clinician has received visual indication that the distal end of the gastric tube 50 has been properly positioned within the GI tract of the patient, an x-ray may be taken to confirm the location of the gastric tube 50. Once the clinician believes the gastric tube 50 is properly positioned within the GI tract, the push-pin 76 formed on the housing 22 is pushed into opening 42a to seal the third passageway 42 from the central passageway 36. As discussed above, in some embodiments it is envisioned that the push-pin 76 may be repeatedly received in opening 42a such that the confirmation device 20 may be reused.

Figure 5:
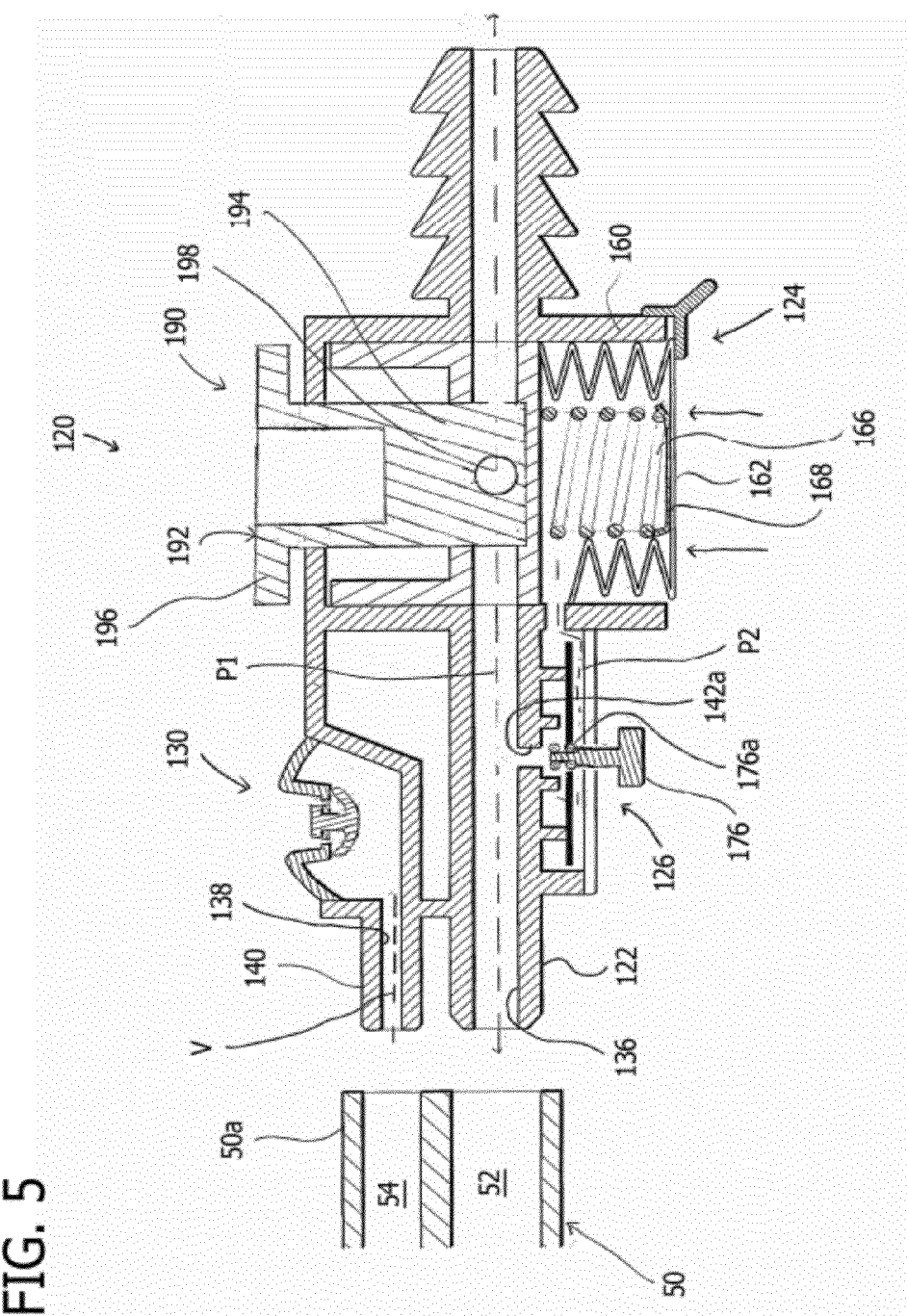
FIG. 5 is a cross section of a confirmation device according to a second embodiment of the present disclosure showing a bellows in a second or compressed condition.
Figure 6:
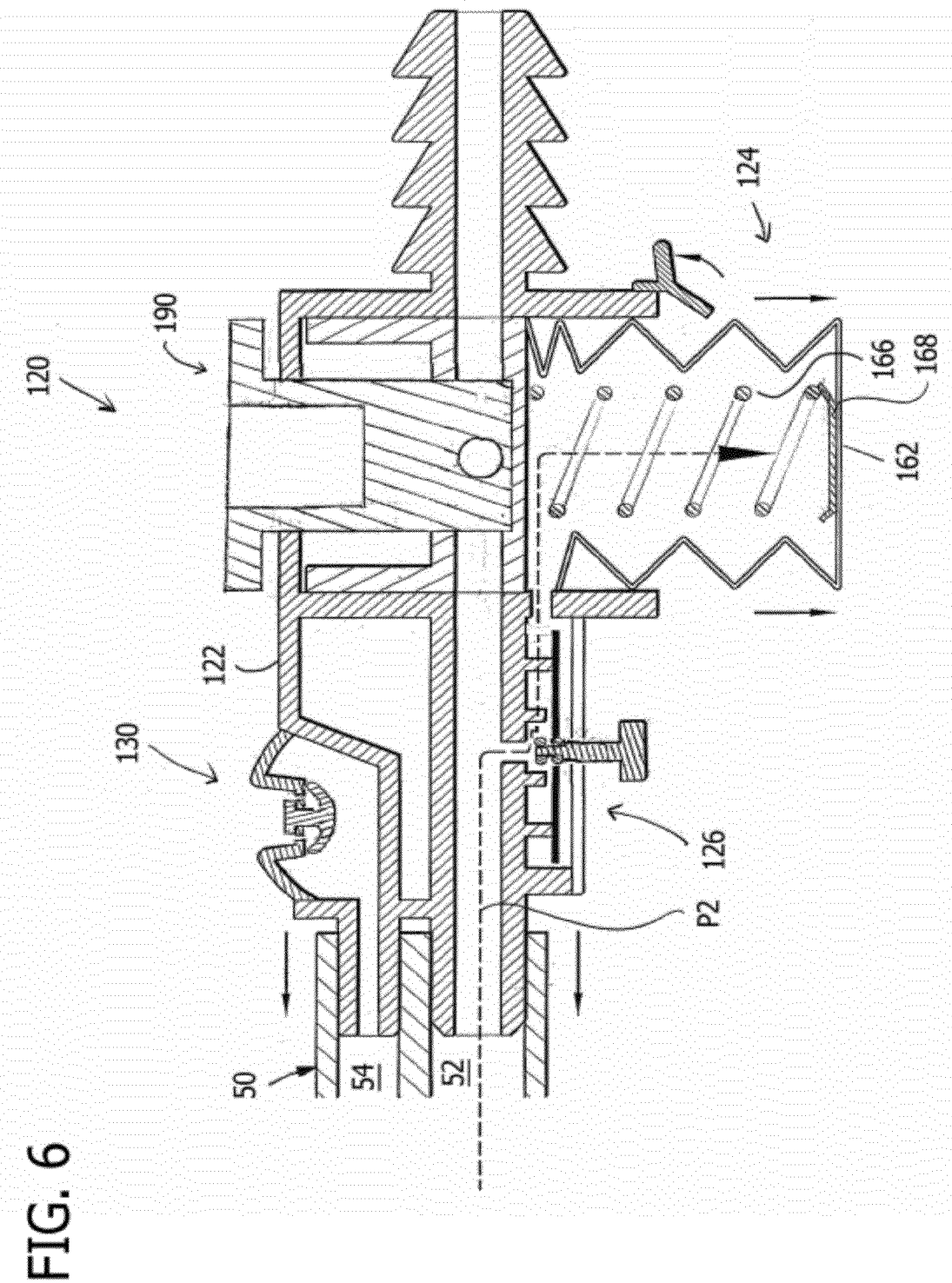
FIG. 6 is a cross section of the confirmation device of the second embodiment showing a bellows assembly in a first or expanded condition and a push pin in an open position.
Figure 7:
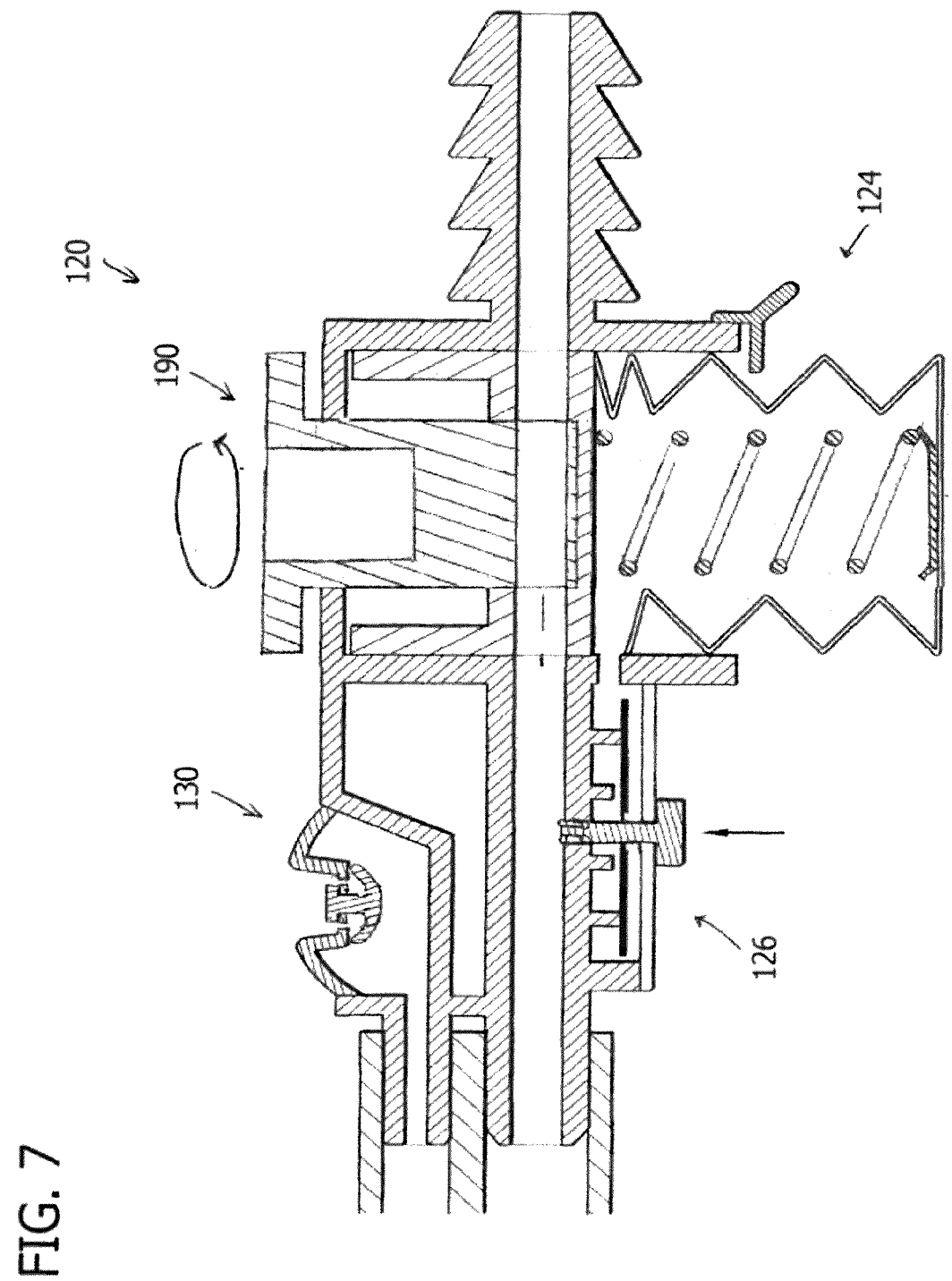
FIG. 7 is a cross section of the confirmation device of the second embodiment showing the bellows assembly in a first or expanded condition and the push-pin in a closed position.

With reference now to FIGS. 5-7, an alternative embodiment of a confirmation device according to the present disclosure is designated in its entirety by the reference 120. Similar reference numerals denote similar structure throughout the embodiments. The confirmation device 120 is substantially similar to the confirmation device 20 described above and therefore only the differences will be described in detail. The confirmation device 120 includes a housing 122, a negative pressure member 124, an indicator assembly 126, a vent mechanism 130, and a passageway obstruction assembly, generally designated by 190.

As shown in FIG. 5, the negative pressure member 124 includes a bellows member 162 as described above further including a biasing member 166 operatively received in the bellows member. As shown, the biasing member 166 includes a spring extending the length of the bellows member 162. Alternatively, the biasing member may include a piston, compressible foam, or other biasing mechanism to selectively expand the bellows member 162. The spring 166 includes a rigid spring pad 168 configured to engage a distal end 162b of bellows member 164. By including the biasing member 166 inside the bellows member 164, the bellows member may be constructed of a thinner material. The negative pressure member 124 operates similarly to the negative pressure member 24 described above.

Still referring to FIG. 5, indicator assembly 130 includes a selectively positionable push-pin 176 configured to selectively block the opening 142a formed in the housing 122. The push-pin 176 includes a pair of O-rings 176a configured to selectively engage the opening 142a. In this manner, the push-pin 176 may be selectively removed from the opening 142a so the confirmation device 120 may be reused.

As shown in FIG. 5, the passageway obstruction assembly 190 includes a stopcock valve 192 having a base portion 194 and a handle portion 196. The base portion 194 is configured to be received within the housing 122 of the confirmation device 120 and includes a passage 198 configured to align with the central passageway 136 when the stopcock valve 192 is in a second or open position. The handle portion 196 extends from the housing 122 and is configured to facilitate manipulating the assembly 190 by hand. Rotating the stopcock valve 192 selectively aligns the passage 198 with the central passageway 136 of the housing 122. In this manner, the primary flowpath P1 may be selectively blocked.

Figure 8:
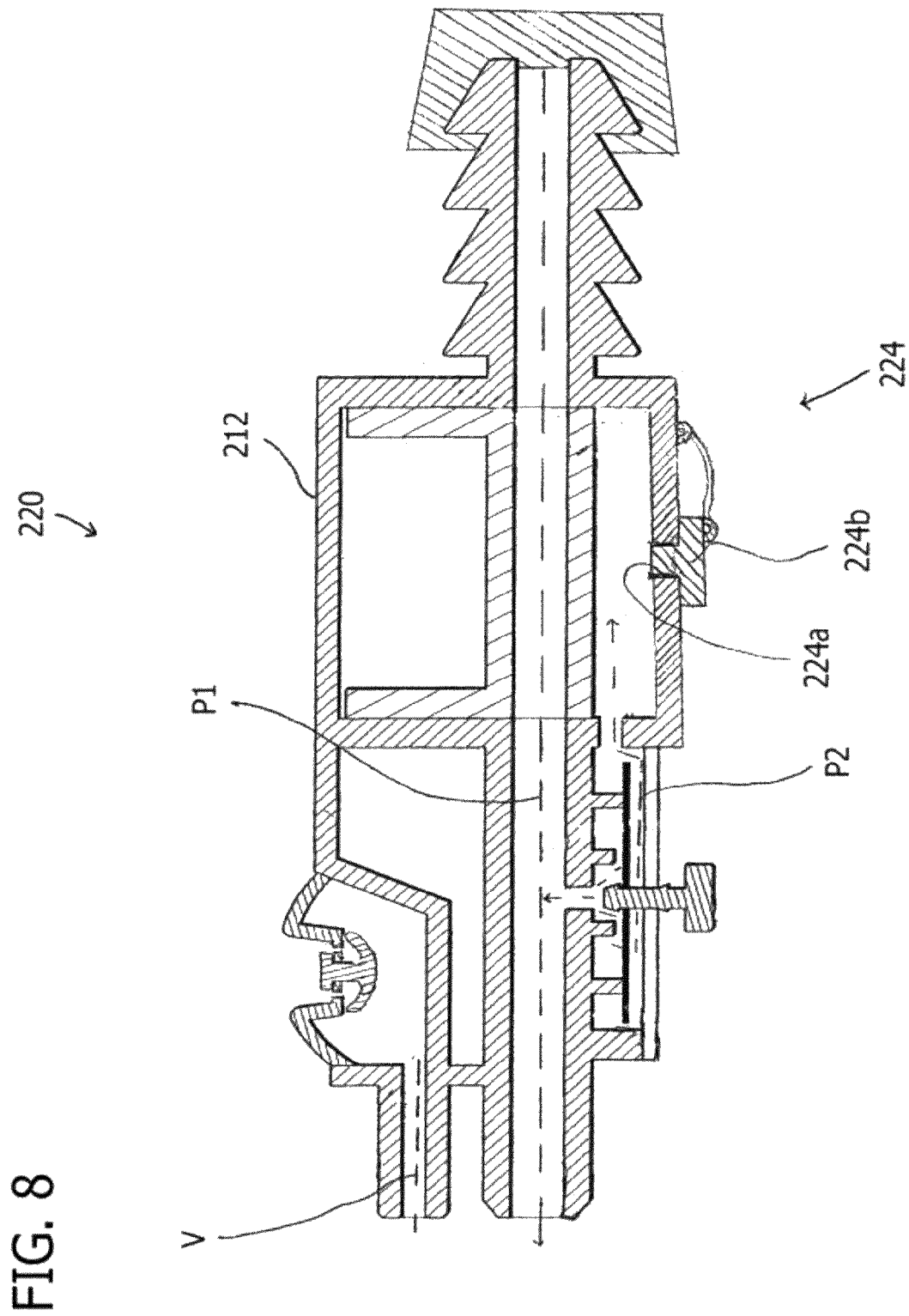
FIG. 8 is a cross section of the confirmation device of a third embodiment.

With reference to FIG. 8, another embodiment of a confirmation device according to the present disclosure is designated in its entirely by the reference 220. The confirmation device 220 is similar to the confirmation devices 20 and 120 described above. Thus, only the differences between the confirmation device 220 and the previously described devices will be discussed. The confirmation device 220 includes a housing 222 having a negative pressure attachment mechanism, generally designated by 224. The negative pressure attachment mechanism 224 includes an opening 224a formed in the housing 222 configured to operably receive a negative pressure source (not shown). The opening 224a may be configured to operably engage a syringe, squeeze ball or other vacuum source (not shown). The negative pressure attachment mechanism 224 may include a cap member 224b configured to selectively seal the opening 224a.

Figure 9:
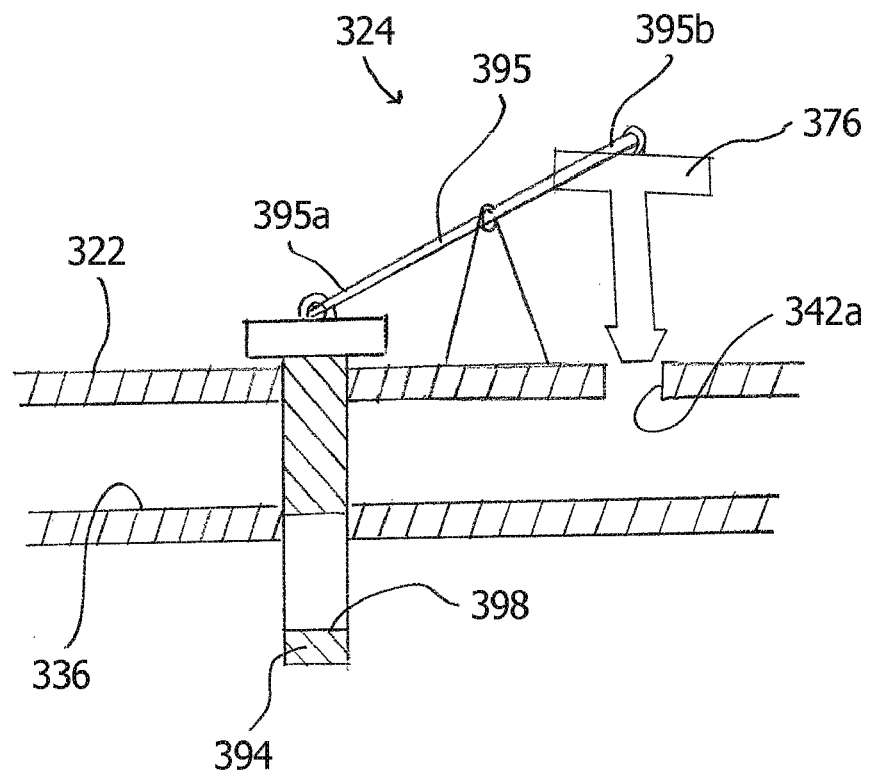
FIG. 9 is a fragmentary cross section of a fourth embodiment of a passageway obstruction device according to the present disclosure, in a first or unobstructed position.
Figure 10:
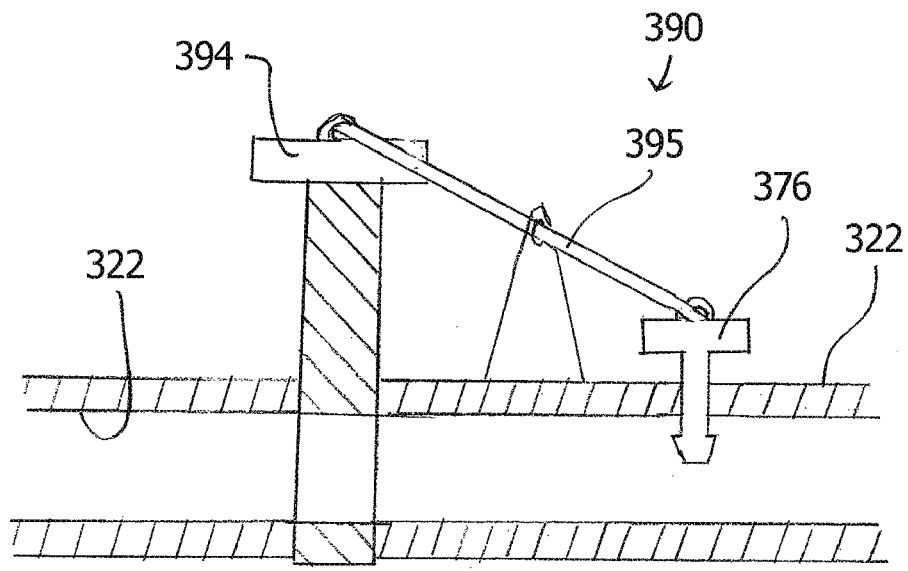
FIG. 10 is a fragmentary cross section of the passageway obstruction of the third embodiment, in a second or obstructed position.

With reference now to FIGS. 9 and 10, an alternative embodiment of a passageway obstruction assembly is designated generally by 390. The passageway obstruction assembly 390 is configured to selectively obstruct the central passageway 336 of the housing 322. The passageway obstruction assembly 390 is further configured to selectively seal an opening 342a formed in the housing 322. As described in detail above, the opening 342a fluidly communicates the central passageway 336 with a third passageway (not shown). The passageway obstruction assembly 390 includes an obstruction member 394 operably connected to a first end 395a of a lever member 395. The passageway obstruction assembly 390 further includes a push-pin 376 operably connected to a second end 395b of the lever 395. The lever 395 is pivotally mounted on a fulcrum member 397 extending from the housing 322. The obstruction member 394 includes a passage 398 configured to be aligned with the central passageway 336 when the passageway obstruction assembly 390 is in a second or unobstructed position.

With reference still to FIGS. 9 and 10, the lever 395 is configured to move between a first position (FIG. 9) in which the passage 398 in obstruction member 390 is not aligned with the central passageway 336 and a second position (FIG. 10) in which the passage is aligned with the central passageway. In the first position, the opening 342a is open, permitting flow from the central passageway 336 into the third passageway (not shown). In the second position, the push-pin 376 blocks the opening 342a to seal the opening and prevent flow into the third passageway.

Figure 11:
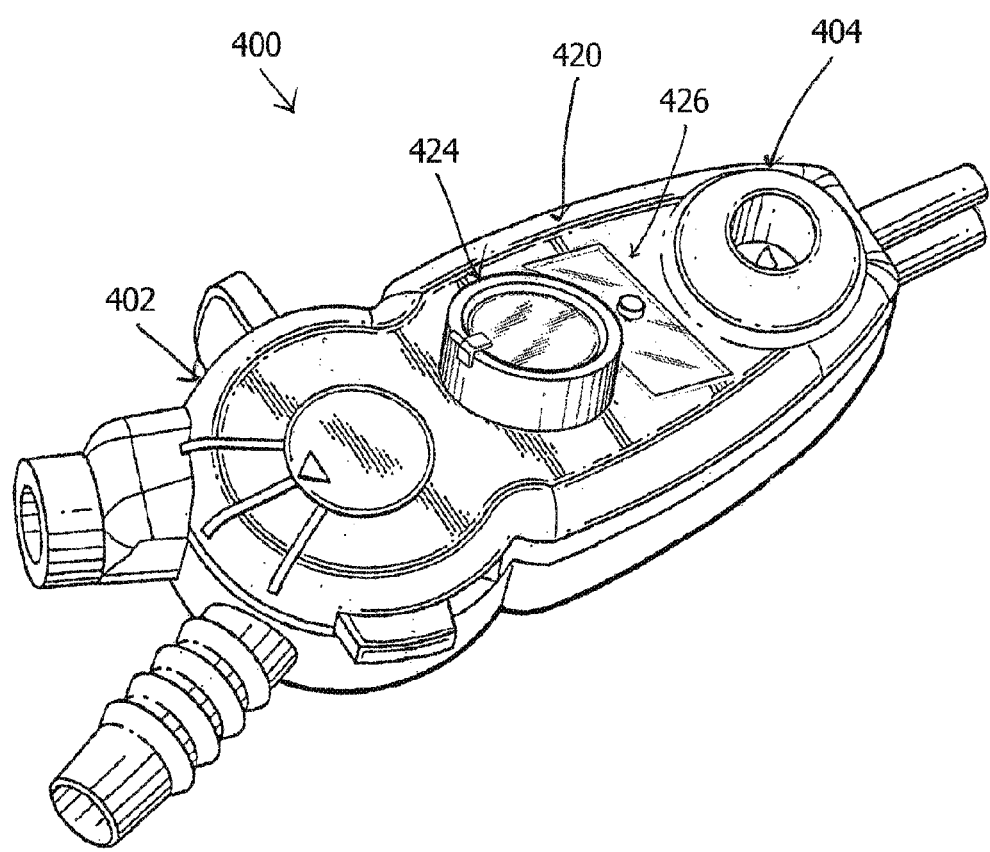
FIG. 11 is a perspective of a valve assembly including an embodiment of a confirmation device according to the present disclosure.

As shown in FIG. 11, an alternate embodiment of a confirmation mechanism of the present disclosure, designated generally by 420, may be combined with a valve assembly 400. The valve assembly 400 is substantially similar to valve assemblies disclosed in commonly owned U.S. Patent Application Publication No. 2006/0122559, which is incorporated by reference in its entirety. The valve assembly 400 includes a valve mechanism 402 and a vent assembly 404. The valve assembly 400 further includes a confirmation mechanism 420 integrally formed with it. The confirmation mechanism 420 is substantially similar to the confirmation devices 20, 120 described above, including a bellows mechanism 424 and an indicator mechanism 426. The bellows mechanism 424 and/or indicator mechanism 426 may be formed on the same or opposite sides of the valve assembly 400. In one embodiment, the bellows mechanism 424 may be formed in alignment with valve member 402. Although the confirmation mechanism 420 may include a vent mechanism (not shown), a vent mechanism is not necessary because the valve assembly 400 includes the vent assembly 404. The confirmation mechanism 420 operates in a substantially similar manner to the confirmation devices 20, 120.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, the color changing member may be replaced with another material capable of acting as a visual indicator in the presence of another fluid or molecule. Furthermore, it is envisioned that the vent assembly may include pressure sensitive flaps or other release mechanisms for venting excess pressure from within the GI tract.

It will be understood that various modifications may be made to the embodiments disclosed herein. Therefore, the above description should not be construed as limiting, but merely as examples of preferred embodiments. Those skilled in the art will envision other modifications within the scope and spirit of the claims appended hereto.

When introducing elements of the present invention or the preferred embodiments(s) thereof, the articles "a", "an", "the", and "said" are intended to mean that there are one or more of the elements. The terms "comprising", "including", and "having" are intended to be inclusive and mean that there may be additional elements other than the listed elements.

What is claimed is:

1. A confirmation device comprising:
   a housing having a central passageway and a secondary passageway extending from an opening in the central passageway to an opening in a bellows receptacle formed in the housing;
   a bellows mechanism in communication with the secondary passageway and including a bellows received in the bellows receptacle in the housing and forming with the bellows receptacle an expandable and collapsible volume in communication with the secondary passageway through the opening in the bellows receptacle; and
   an indicator mechanism in fluid communication with the secondary passageway for visually indicating the presence of one or more components within the fluid flow in the secondary passageway, wherein the indicator mechanism includes a color changing member configured to change color in the presence of one or more components and the bellows assembly is operable to draw fluid across the indicator mechanism.

2. A confirmation device as set forth in claim 1 wherein the housing is configured to be operably connected to gastric tubing.

3. A confirmation device as set forth in claim 2 wherein the housing has first and second distal connectors for engaging first and second lumens in the gastric tubing.

4. A confirmation device as set forth in claim 1 wherein the housing has a vent passageway communicating with the second distal connector, and the device further includes a vent mechanism for enabling passage of ambient air into the vent passageway.

5. A confirmation device as set forth in claim 4 wherein the vent mechanism is configured to release excess pressure from within the GI tract of a patient.

6. A confirmation device as set forth in claim 1 further comprising an obstruction assembly configured to selectively obstruct the central passageway.

7. A confirmation device as set forth in claim 6 wherein the obstruction assembly includes a stopcock valve.

8. A confirmation device as set forth in claim 6 wherein the obstruction assembly includes an end cap.

9. A confirmation device as set forth in claim 1 wherein the color changing member is configured to change to a first color in the presence of a first component.

10. A confirmation device as set forth in claim 9 wherein the color changing member is configured to change to a second color in the presence of a second component.

11. A confirmation device as set forth in claim 1 wherein the bellows is affixed to a portion of the housing.

12. A confirmation device as set forth in claim 1 wherein the housing includes a color scale for referencing a meaning of the color change.

13. A confirmation device as set forth in claim 1 wherein the housing includes a clear portion for viewing the indicator mechanism.

14. A confirmation device as set forth in claim 1 wherein the housing is integrally formed with a valve assembly.

* * * * *